Figure 1:
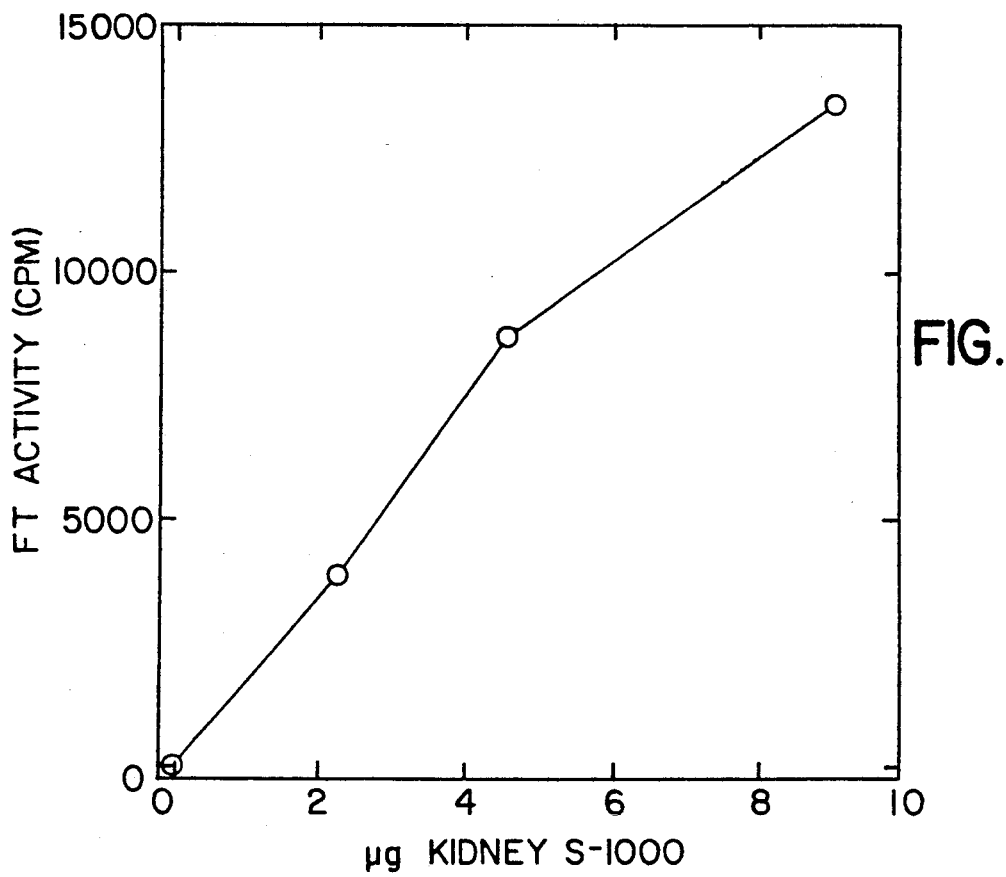

United States Patent [19]

Barbacid et al.

[11] Patent Number: 5,185,248
[45] Date of Patent: Feb. 9, 1993

[54] FARNESYL-PROTEIN TRANSFERASE ASSAY FOR IDENTIFYING COMPOUNDS THAT BLOCK NEOPLASTIC TRANSFORMATION

[75] Inventors: Mariano Barbacid, Lawrenceville, N.J.; Veeraswamy Manne, Philadelphia, Pa.

[73] Assignee: E. R. Squibb & Sons, Inc., Princeton, N.J.

[21] Appl. No.: 520,570

[22] Filed: May 8, 1990

[51] Int. Cl.$^5$ .......................... C12Q 1/48; C12N 9/10
[52] U.S. Cl. ...................... 435/15; 435/193; 530/330
[58] Field of Search ............... 435/15, 193; 530/330

[56] References Cited

U.S. PATENT DOCUMENTS 5,043,268 8/1991 Stock .................................. 435/15

OTHER PUBLICATIONS

Goodman, L. E. et al., Yeast 4, 271–281 (1988) "Structure and Expression of Yeast DPR1, a Gene Essential for the Processing and Intracellular Localization of ras Proteins".
Hancock et al., Jun. 30, 1989, Cell 57: 1167–1177.
Casey et al., Nov. 1989, Proc. Natl. Acad. Sci. USA 86: 8323–8327.
Schafer et al., Jul. 1989, Science 245: 379–385.
Goldstein & Brown, Feb. 1990, Nature 343: 425–430.
Touchette, Apr. 1990, J. NIH Res. 2: 61–65.
Jackson et al., Apr. 1990, Proc. Natl. Acad. Sci. USA 87: 3042–3046.
Manne et al., Oct. 1990, Proc. Natl. Acad. Sci. USA 87: 7541–7545.

Primary Examiner—Ronald W. Griffin
Assistant Examiner—Ralph Gitomer
Attorney, Agent, or Firm—James M. Bogden

[57] ABSTRACT

Assays for farnesyl-protein transferase (FT) which can be used to identify substances that block the farnesylation of ras oncogene products are described. Because farnesylation is required for ras oncogene activity, inhibitory compounds identified in the assays of the invention can block neoplastic transformation mediated by the ras oncogene. The assays of the invention are targeted for a step subsequent to the synthesis of farnesyl pyrophosphate (FPP), the donor of the farnesyl residue, and an intermediate in cholesterol synthesis and other important cellular pathways. Therefore, compounds which inhibit ras mediated transformation, yet do not cause major disruptions of important cell pathways that require FPP as an intermediate may be identified using the assays of the invention.

19 Claims, 7 Drawing Sheets

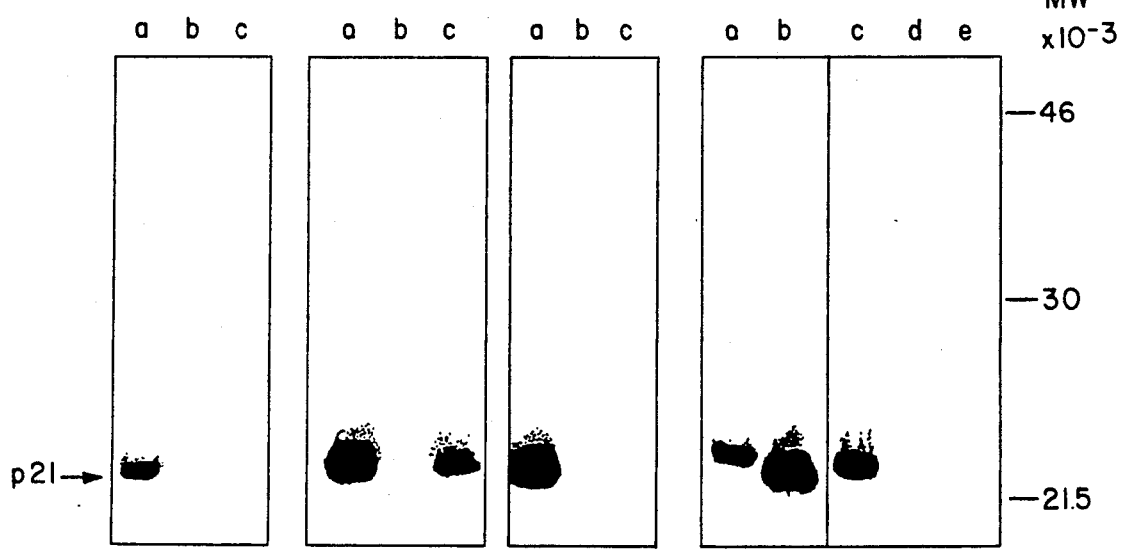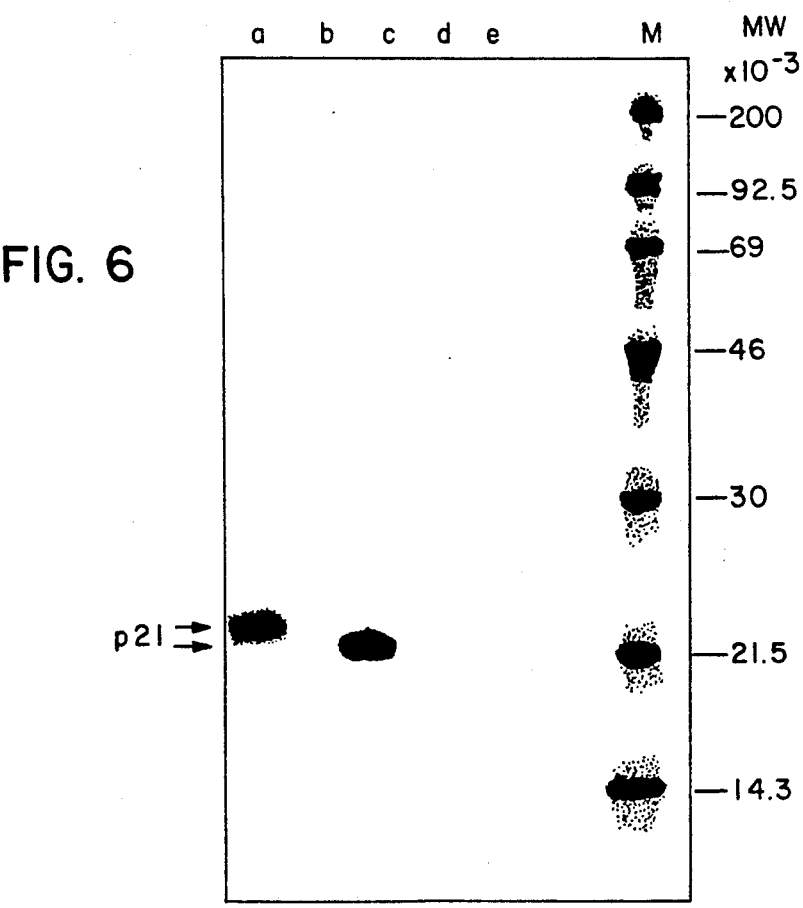

FARNESYL-PROTEIN TRANSFERASE ASSAY FOR IDENTIFYING COMPOUNDS THAT BLOCK NEOPLASTIC TRANSFORMATION

TABLE OF CONTENTS

1. Introduction
2. Background Of The Invention
3. Summary Of The Invention
   3.1. Definitions
4. Description Of The Figures
5. Detailed Description Of The Invention
   5.1. The Assay Components And Reaction Conditions
   5.2. The Farnesyl-Protein Transferase Assay
6. Example: Assay For Farnesyl-Protein Transferase
   1. Materials And Methods
      6.1.1. Purification Of H-ras p21 Proteins
      6.1.2. Cell And Organ Extracts
   6.2. Assays For Farnesyl Transferase Activity
      6.2.1. SDS-PAGE Assay
      6.2.2. Filter Binding Assay
   6.3. Results
      6.3.1. In Vitro Farnesylation Of H-ras p21 Proteins
      6.3.2. Chararacterization Of Farnesyl-Protein Transferase Activity
      6.3.3. Specificity Of H-ras p21 Farnesylation
      6 3.4. Farnesyl-Protein Transferase Activity In Mammalian Cells And Tissues
7. Example: Purification Of Farnesyl Protein Transferase
   7.1. Partial Purification Of Farnesyl Protein Transferase From Porcine Kidney: DE-52 Chromatography
   7.2. Partial Purification Of Farnesyl Protein Transferase From Porcine Kidney: Gel Filtration

1. INTRODUCTION

The present invention relates to assays for farnesyl-protein transferase (FT) that can be used to identify compounds that block the farnesylation of ras oncogene products. Because farnesylation is required for ras oncogene activity, FT inhibitory compounds identified in the assays of the invention can block neoplastic transformation mediated by the ras oncogene. The assays of the invention are targeted for a step subsequent to the synthesis of farnesyl pyrophosphate (FPP), the donor of the farnesyl residue, and an intermediate in cholesterol synthesis and other important cellular pathways. Therefore, compounds which inhibit ras mediated transformation, yet do not cause major disruptions of important cell pathways that require FPP as an intermediate, may be identified using the assays of the invention.

2. BACKGROUND OF THE INVENTION

Genetic studies first established that ras p21 proteins require a defined carboxy-terminal structure to exert their biological function. This structure, known as the CAAX box, consists of a conserved cysteine residue located at position 186 (except in the K-ras4B p21 protein, in which cysteine is located at position 185), two aliphatic amino acids and any carboxy-terminal amino acid residue. Mutations affecting the basic CAAX box structure of oncogenic ras p21 proteins completely abolish their transforming activity, presumably by impeding their interaction with the inner side of the plasma membrane. Such interaction requires a series of post-translational modifications within the CAAX box motif which include (a) farnesylation of the $Cys^{186}$ residue; (b) cleavage of the three carboxy-terminal amino acid residues; and (c) methylation of the free carboxyl group generated in the resulting carboxy-terminal farnesyl-cysteine residue. The interaction of these farnesylated ras p21 proteins with cellular membranes is further strengthened by palmitoylation of neighboring upstream cysteine residues. See Hancock, et al., Jun. 30, 1989, Cell 57: 1167–1177; and Casey, et al., November 1989, Proc. Natl. Acad. Sci. U.S.A. 86: 8323–8327.

Recent studies have suggested that the donor of the farnesyl residue present in ras p21 proteins is likely to be FPP, a precursor in the biosynthesis of cholesterol. Treatment of S. cerevisiae cells or Xenopus oocytes with inhibitors of HMG-CoA reductase, the enzyme responsible for the synthesis of mevalonic acid, the precursor of isoprenoid compounds, blocks the function of ras proteins in these cells. These results have raised the possibility of using available inhibitors of cholesterol biosynthesis to block neoplastic transformation induced by ras oncogenes. See, Schafer, et al., Jul. 28, 1989, Science 245: 379–385; and Goldstein and Brown, Feb. 1, 1990, Nature 343: 425–430. However, FPP is not only an intermediate in the biosynthesis of cholesterol, but also a precursor of ubiquinones, dolichols and Haem A. Therefore, it is likely that attempts to block ras oncogene function by inhibiting the synthesis of FPP will cause major disruptions in other cellular pathways. For a review, see Touchette, April 1990, J. NIH Res. 2: 61–65.

3. SUMMARY OF THE INVENTION

The present invention relates to assays for farnesyl-protein transferase (FT) activity which can be used to identify compounds that inhibit or block the farnesylation of ras oncogene products, and, therefore, inhibit or block neoplastic transformation mediated by the ras oncogene. The assay of the invention is based, in part, on the discovery and identification of the FT enzyme which catalyzes the transfer of the farnesyl group from the donor, farnesyl pyrophosphate (FPP), to the ras p21 $Cys^{186}$ residue. Farnesylation of ras proteins is required for their attachment to the inner cell membrane and biological activity. Farnesylation of ras oncogene products is required for ras mediated transforming activity. Because the assays of the present invention are designed to target a step subsequent to the synthesis of FPP, they allow for the identification of compounds that interfere with farnesylation of the ras oncogene products and inhibit their transforming activity, yet do not interfere with the synthesis of FPP, a precursor in the synthesis of cholesterol, ubiquinones, dolichols and Haem A. Therefore, inhibitory compounds that do not disrupt important cellular pathways which require FPP may be identified using the assay of the present invention.

The invention is demonstrated by way of examples which describe assays that can be used to identify compounds that interfere with FT activity; a characterization of FT activity; as well as the identification and partial purification of FT capable of farnesylating ras p21 proteins.

3.1. DEFINITIONS

The following terms, as used herein, will have the meanings indicated.

| | |
|---|---|
| DTT = | dithiothreitol |
| EDTA = | etheylenediaminetetraacetic acid |
| EGTA = | ethylene glycol bis (β-aminoethyl-ether) N,N,N',N'-tetraacetic acid |
| FPP = | farnesyl pyrophosphate |
| FT = | farnesyl protein transferase |
| HMG CoA reductase = | 3-hydroxy-3-methylglutaryl coenzyme A reductase |
| PMSF = | phenylmethylsulfonyl fluoride |
| SDS-PAGE = | sodium dodecylsulfate polyacrylamide gel electrophoresis |

4. DESCRIPTION OF THE FIGURES

FIG. 1. FT activity in crude extracts of porcine kidney as detected by a filter binding assay. Reactions were carried out at 37° C. for 1 hour in the presence of 1 μg of a partially-purified H-ras p21N, 0.2 μCi of [$^3$H]FPP (specific activity 20 Ci/mmol), 25 mM Mg$^{2+}$ and 10 mM DTT and the indicated amounts of porcine kidney S-100 fraction. Experimental conditions were those described in Section 6, infra.

Figure 2:
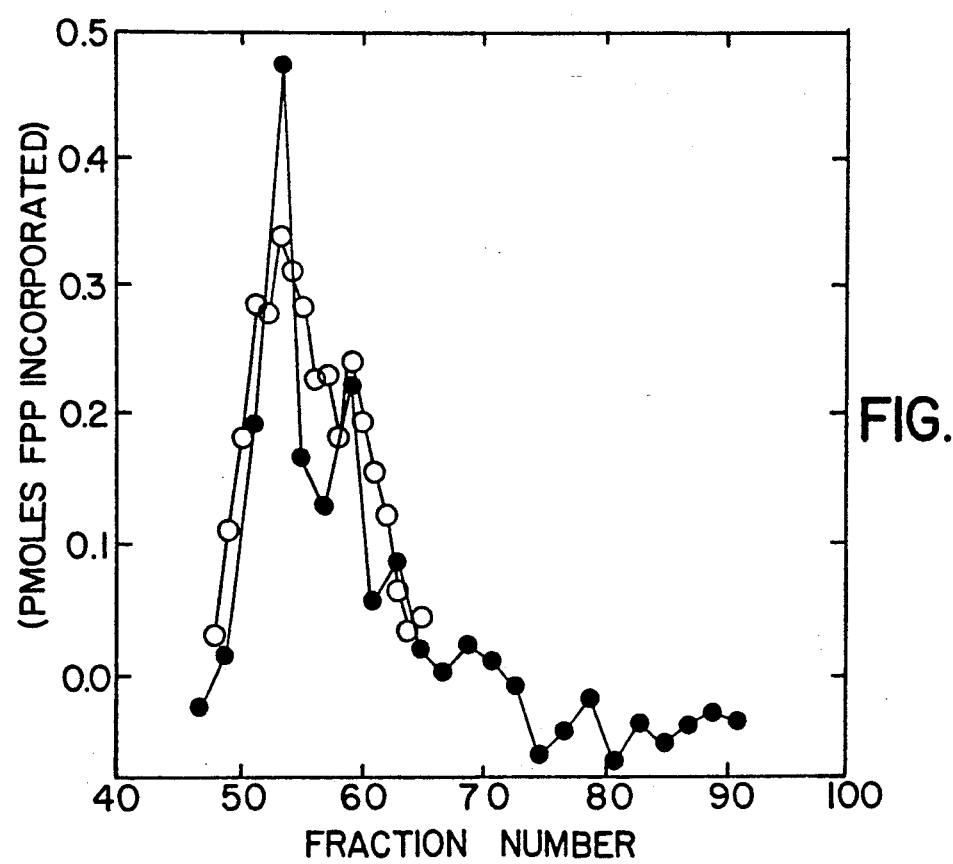
Figure 4A:
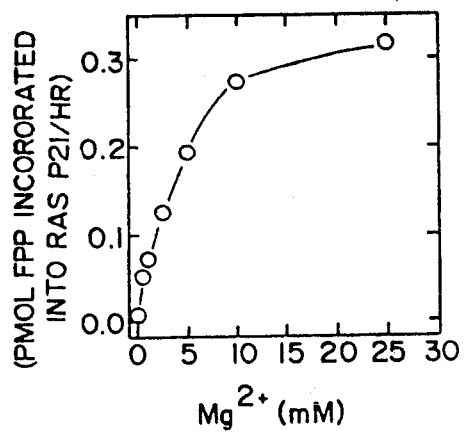
Figure 4B:
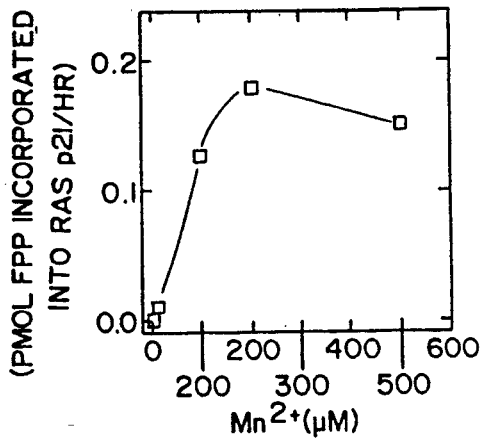
Figure 4C:
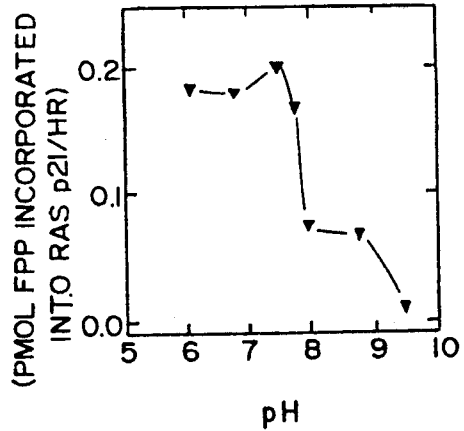
Figure 4D:
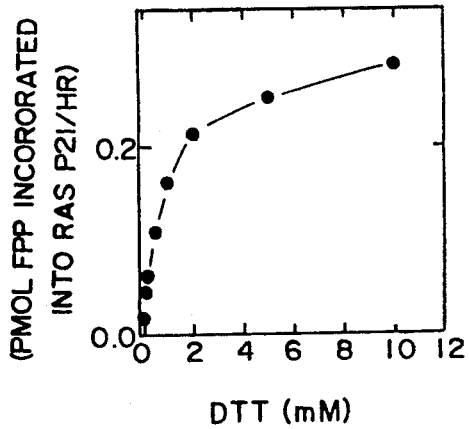

FIG. 2. Detection of FT activity by SDS-PAGE (open circles) and the filter binding technique (closed circles). Comparative analysis of the detection of FT activity in partially purified extracts of porcine kidney fractionated by gel filtration chromatography (Sephacryl S-200). Experimental conditions were those described in Section 6, infra.

FIG. 3. In vitro farnesylation of ras p21 proteins analyzed by SDS-PAGE. Unless stated otherwise, reactions were carried out at 37.C for 1 hour in the presence of 1 μg of a partially-purified H-ras p21N, 20 μg of various lysates of human TT cells, 0.2 μCi of [$^3$H]FPP, 5 mM Mg$^{2+}$ and 5 mM DTT.

FIG. 3A. Incorporation of [3H]FPP into ras p21 is dependent on the presence of ras p21 protein and an FT enzyme source: lane a, complete reaction using a crude lysate of human TT cells; lane b, same as lane a, except ras p21N was omitted; lane c, same as lane a except the TT cell extract was omitted.

FIG. 3B. Subcellular localization of FT activity. Lane a, S-100 fraction; lane b, P-100 fraction; lane c, total lysate.

FIG. 3C. FT activity is heat labile and can be blocked with excess non-radioactive FPP: lane a, complete reaction using the S-100 fraction of TT cells; lane b, same as lane a, except S-100 fraction was preincubated at 65° C. for 30 minutes; lane c, same as lane a, except a 100-fold excess of non-radioactive FPP was added to the reaction mixture.

FIG. 3D. Farnesylation of various E. coli-synthesized recombinant proteins by the S-100 fraction of human TT cells: lane a, 1.2 μg of H-ras p21N; lane b, 1 μg of H-ras p21T; lane c, 1 μg H-ras p21H; lane d, 10 μg of IL-2; lane e, 7.5 μg of p75$^{myb}$. In all cases, reactions were terminated by the addition of SDS-PAGE sample buffer and analyzed by SDS-PAGE using 12.5% gels as described in Section 6. Electrophoresed gels were exposed at −70° C. to Kodak X-Omatic AR5 film in the presence of intensifier screens for 1 to 3 days. Co-electrophoresed molecular weight markers (MW) included ovalbumin (46,000 daltons), carbonic anhydrase (30,000 daltons) and trypsin inhibitor (21,500 daltons). The migration of the farnesylated H-ras p21 proteins is indicated by an arrow.

FIG. 4. Effect of (A) Mg$^{2+}$ ions; (B) Mn$^{2+}$ ions; (C) pH and (D) SH-group protecting compounds on FT activity. Reactions were carried out as indicated in the legend to FIG. 1 and analyzed by SDS-PAGE. The amount of radioactivity incorporated into the H-ras p21 proteins was determined by cutting the band from the gel, followed by solubilization and liquid scintillation counting in a Tri-Carb Model 2200 CA (Packard) liquid scintillation counter. Results are expressed as pmoles of FPP incorporated per hour into H-ras p21.

FIG. 5. Kinetics of FT activity.

Figure 5A:
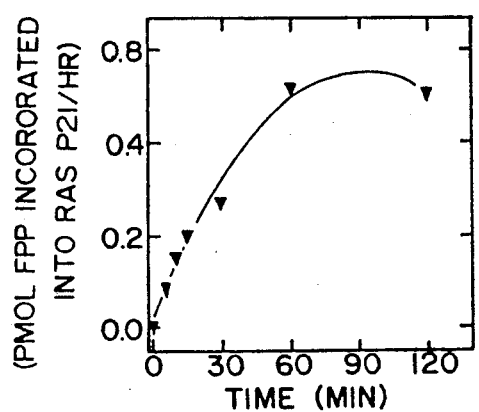

FIG. 5A. Time course curve. A reaction mixture (80 μl) containing 100 mM Hepes, pH 7.4, 5 mM DTT, 25 mM MgCl$_2$, 1 μM [$^3$H]FPP, 1.25 μg of H-ras p21N and 176 μg of TT S-100 fraction was incubated at 37° C. The reaction was terminated by removing, at the indicated intervals, 10 μl aliquots and mixing them with 12 μl of 2× SDS-PAGE sample buffer.

Figure 5B:
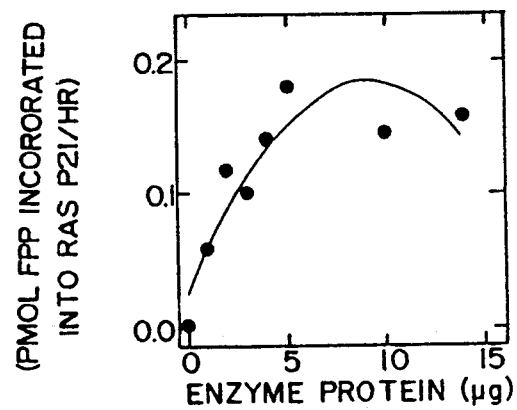

FIG. 5B. Enzyme concentration curve. FT activity was determined by incubating in a final volume of 10 μl the indicated amounts of TT S-100 cell extract with 1.25 μg of H-ras p21N in the presence of 100 mM Hepes, pH 7.4, 5 mM DTT, 25 mM MgCl$_2$ and 1 μM [$^3$H]FPP at 37° C. for 1 hour.

Figure 5C:
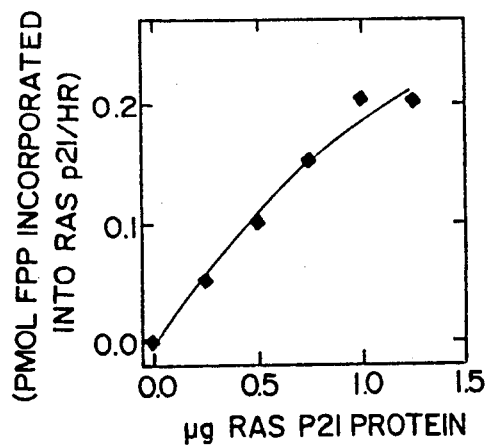

FIG. 5C. H-ras p21 substrate saturation kinetics. FT activity was determined as in FIG. 5B except reactions contained 22 μg of TT S-100 extract and the indicated amounts (0 to 1.25 μg) of H-ras p21N.

Figure 5D:
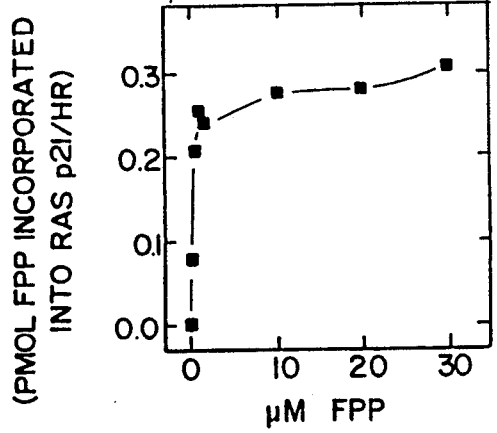

FIG. 5D. FPP substrate saturation kinetics. FT activity was determined as in FIG. 5B in the presence of 1 μg of H-ras p21N protein, 11 μg of TT S-100 extract and the indicated amounts of [$^3$H]FPP. Samples were analyzed by SDS-PAGE as described in the legend to FIG. 1.

FIG. 6. In vitro farnesylation of H-ras p21 proteins occurs at Cys[186] and requires an intact CAAX box motif. Farnesylation of: lane a, H-ras p21H; lane b, pNW858; lane c, pNW739; lane d, pNW754; and lane e, pNW277 proteins (Table 1) was conducted as indicated in the legend to FIG. 3 using 1 μg of each of these proteins and 20 μg of the TT S-100 cell extract. Samples were analyzed by SDS-PAGE as indicated in FIG. 1. Co-electrophoresed molecular weight standards (M) include myosin (200,000 daltons), phosphorylase b (92,500 daltons), bovine serum albumin (69,000 daltons), ovalbumin (46,000 daltons), carbonic anhydrase (30,000 daltons), trypsin inhibitor (21,500 daltons) and lysozyme (14,300 daltons). The migration of farnesylated H-ras p21 proteins is indicated by arrows.

Figure 7:
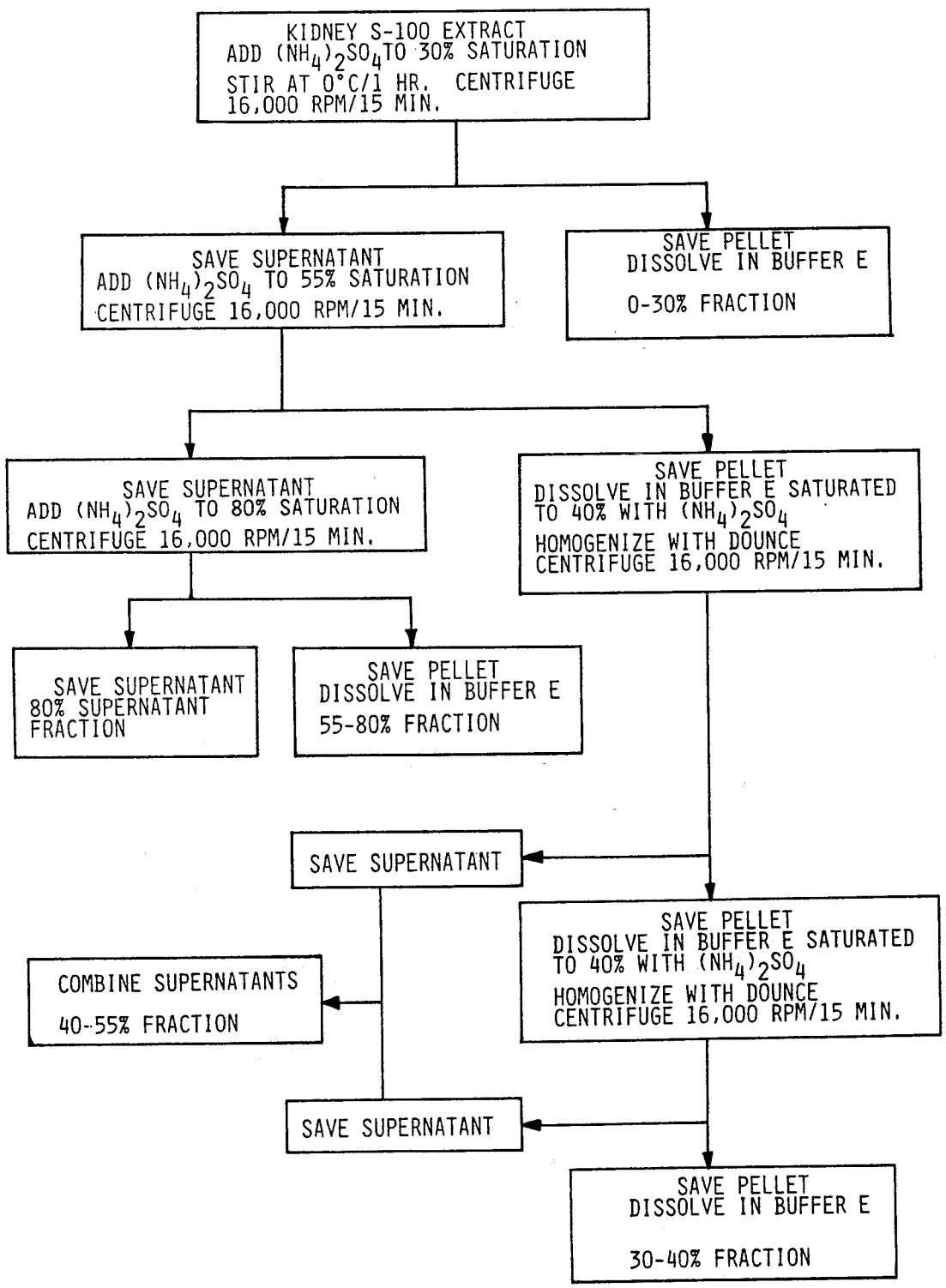

FIG. 7. Scheme for the partial purification of FT from porcine kidney. The figure depicts the ammonium sulfate fractionation step as described in Section 7, infra.

Figure 8:
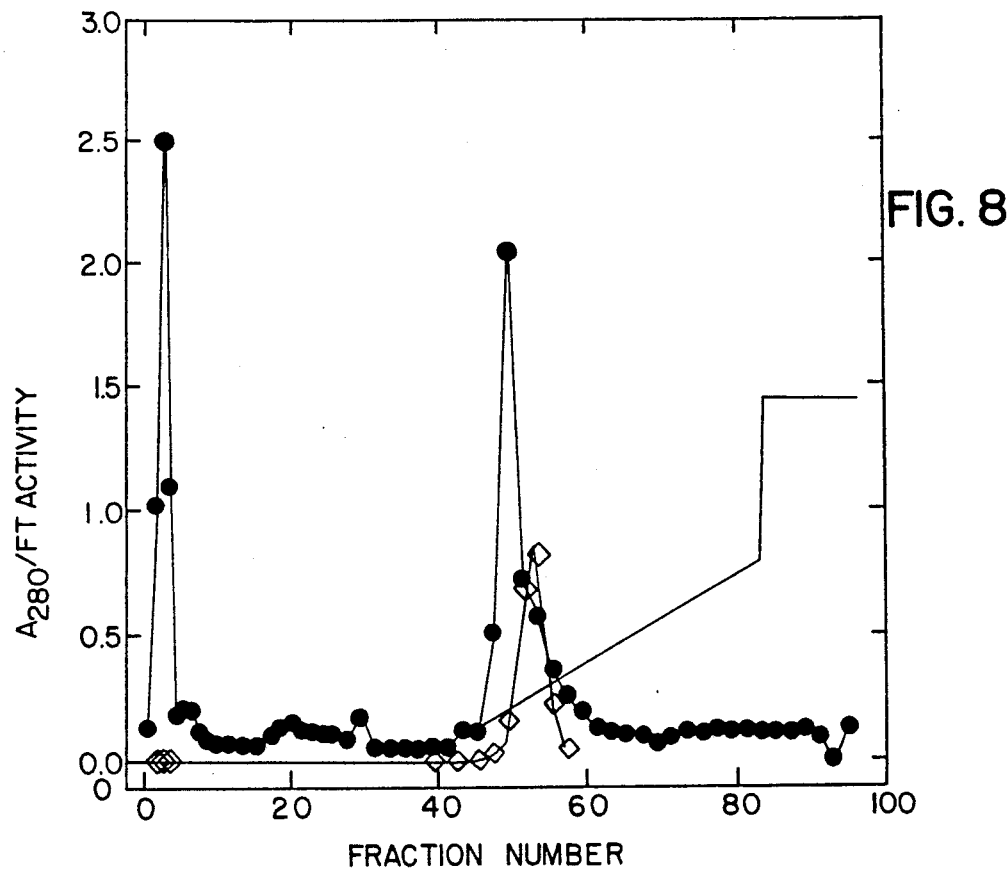

FIG. 8. DE-52 cellulose chromatography of FT from porcine kidney. The 30–40% fraction obtained from (NH$_4$)$_2$SO$_4$ fractionation (see FIG. 7) was extensively dialyzed against buffer E (20 mM Tris HCl, pH 7.4, 1 mM DTT, 0.1 mM EDTA, 0.5 mM PMSF and 5% glycerol) and the precipitated proteins removed by centrifugation. The clear supernatant was loaded onto a DE-52 cellulose column (30 cm ×1.6 cm) equilibrated with buffer E. The column was extensively washed with buffer E until the absorbance at 280 nm (A$_{280}$) returned to base line. Proteins bound to the cellulose matrix were eluted with a 0 to 0.6 M linear gradient of NaCl, followed by a solution of 1 M NaCl, each in buffer E. Fractions (8 ml) were collected and their protein content determined by A$_{280}$ (closed symbols). Aliquots (3 μl) were assayed for FT activity by the SDS-PAGE assay (open symbols).

Figure 9:
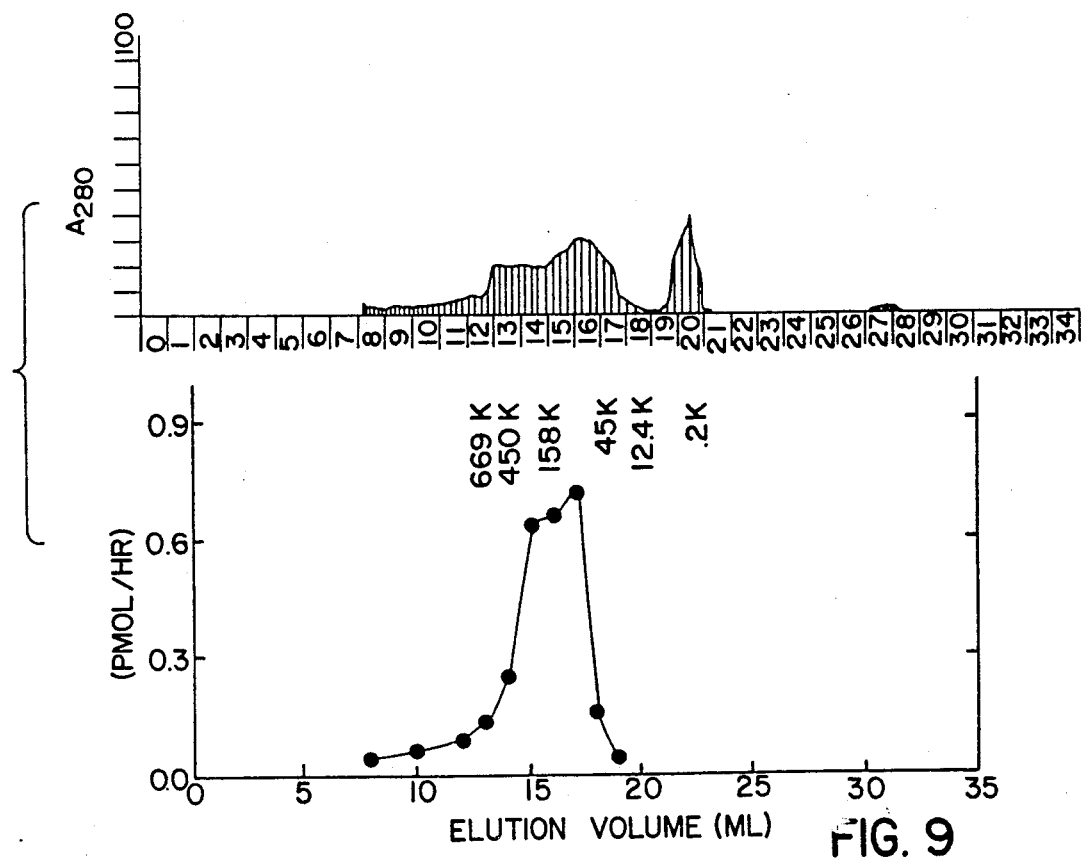

FIG. 9. Superose 6 gel filtration chromatography of FT from porcine kidney. Fractions from the DE-52 cellulose column containing FT activity were pooled and concentrated by filtration through an Amicon YM-10 membrane until reaching a protein concentration of 7 mg/ml. 0.2 ml (1.4 mg) of this concentrated sample was loaded onto a Superose 6 HR 10/30 column previously equilibrated with buffer F (50 mM sodium phosphate buffer, pH 7.0, containing 200 mM NaCl, 1 mM DTT and 5% glycerol). The loaded sample was eluted with the same buffer at a flow rate of 0.2 ml/minute. The eluant was monitored for protein using an UV-M detector. 0.2 ml fractions were collected and 3 µl aliquots assayed for FT activity by the SDS-PAGE assay as described in Section 6, infra. The upper panel shows the protein elution profile as determined by $A_{280}$. The lower panel shows enzymatic activity. The positions of the molecular weight calibration markers, chromatographed under similar conditions, are indicated. They include thyroglobulin (669,000 daltons), ferritin (450,000 daltons), aldolase (158,000 daltons), ovalbumin (45,000 daltons), cytochrome C (12,400 daltons) and glycyl-tyrosine (238 daltons).

Figure 10:
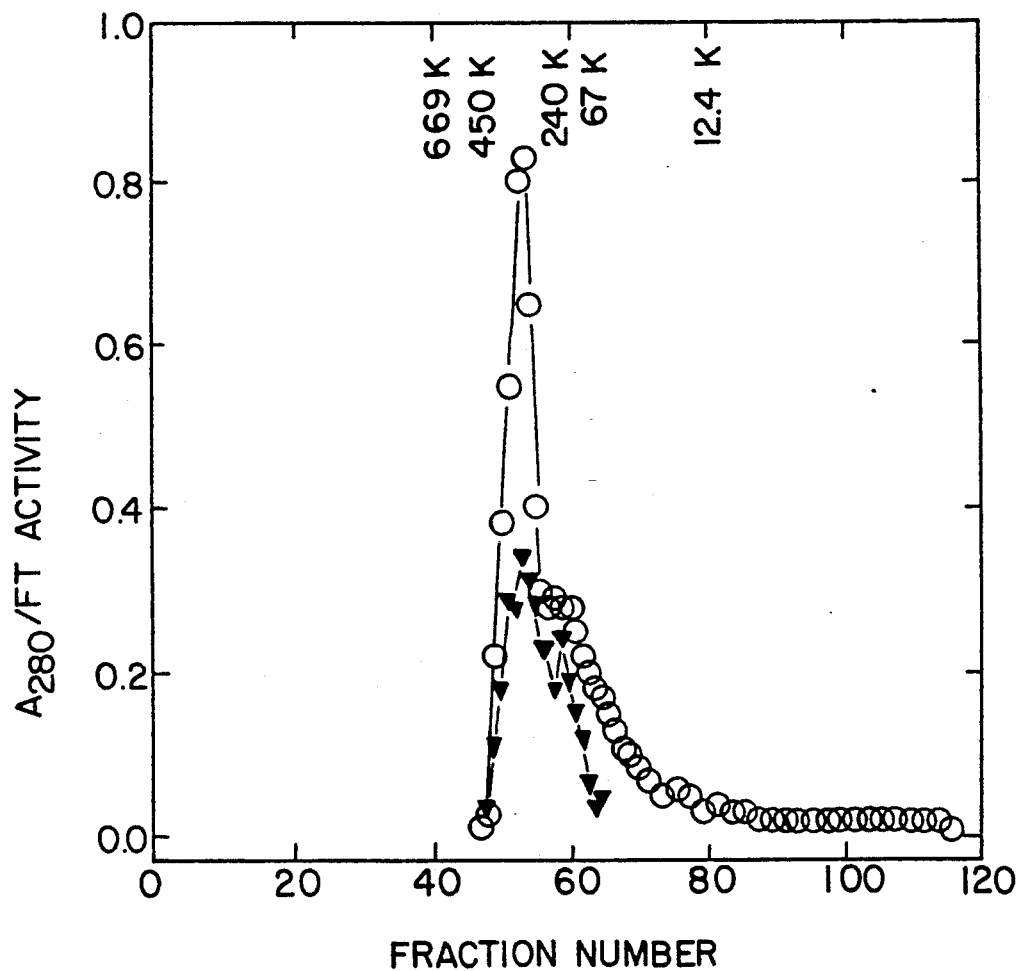

FIG. 10. Sephacryl S-200 gel filtration chromatography of FT from porcine kidney. Fractions from the DE-52 cellulose column containing FT activity were pooled and concentrated as indicated in the legend to FIG. 9. One ml (7 mg) of this concentrated sample were loaded onto a Sephacryl S-200 HR column equilibrated with buffer F (see legend to FIG. 9). The loaded sample was eluted with buffer F at a flow rate of 14 ml/hour and collected in 1.59 ml fractions. Total protein (open symbols) and FT activity (closed symbols) were assayed as indicated in the legend to FIG. 8. The positions of the molecular weight calibration markers, chromatographed under similar conditions, are indicated. They include thyroglobulin (669,00 daltons), ferritin (450,000 daltons), catalase (240,000 daltons), bovine serum albumin (67,000 daltons) and cytochrome C (12,400 daltons).

5. DETAILED DESCRIPTION OF THE INVENTION

The farnesylation of ras proteins is required for their biological activity, i.e., the anchoring of the ras protein to the inner side of the plasma membrane and its role in signal transduction. Farnesylation of ras oncogene products is required for ras mediated transformation of normal cells into cancer cells. The transfer of the farnesyl group from FPP, the donor molecule, to ras proteins is hypothesized to be mediated by an enzyme, FT. This putative enzyme has not heretofore been identified, isolated or characterized. The present invention describes assays designed to detect such FT activity by measuring farnesylation of appropriate substrates such as unprocessed ras oncogene products. These assays can be used to identify substances that inhibit farnesylation and ras mediated transformation. In the assays of the invention, a peptide or protein having the required CAAX box motif (hereinafter referred to as the "CAAX-substrate") may be reacted with FPP (the donor of the farnesyl residue, the second substrate) in the presence of the enzyme, FT. Incorporation of the farnesyl residue into the CAAX-substrate is an indication of farnesylation and FT activity. Inhibition of the incorporation of the farnesyl residue by a test substance added to the reaction mixture indicates the ability of the test substance to block farnesylation of ras products and inhibit the transforming biological activity of ras oncogene products.

In the assays of the invention, incorporation of the farnesyl group into the CAAX-substrate may be detected by a variety of methods. For example, farnesylation of the CAAX-substrate can be detected by a change in the mobility of the reaction product as determined by chromatographic methods, including but not limited to TLC (thin layer chromatography), HPLC (high performance liquid chromatography), etc.; or electrophoretic methods such as SDS-PAGE. Additionally, either substrate, the CAAX-substrate or FPP, may be labeled so that detection of the label in the reaction product can be used as an indicator of farnesylation and FT activity. To this end, a variety of signal generating compounds including but not limited to radiolabels, fluorogenic compounds, colorimetric compounds, enzymes, etc. may be incorporated into either substrate using standard metabolic labeling techniques or chemical conjugating techniques. The assay of the invention and its components are described in more detail in the subsections below.

5.1. THE ASSAY COMPONENTS AND REACTION CONDITIONS

The CAAX-substrate, the FPP donor, and the FT enzyme which form the components of the reaction of the assay may be obtained in a variety of ways. The CAAX-substrate may comprise any peptide or protein which has the required CAAX box motif. Such CAAX-substrates may include, but are not limited to unprocessed ras proteins (as used herein, "unprocessed ras proteins" refers to ras proteins which have not been posttranslationally modified by the addition of a farnesyl residue, i.e., unfarnesylated ras proteins), peptides corresponding to the carboxy terminus of unprocessed ras proteins, or any peptide containing the CAAX box motif. Indeed, we have found that peptides comprising the CAAX box plus two additional residues will function as a CAAX-substrate in the assays of the invention.

Unprocessed ras proteins which can be used as the CAAX-substrate may advantageously be obtained by cloning and expressing the ras oncogene or protooncogene (Barbacid, 11987, Ann. Rev. Biochem. 56: 779-827) or mutants thereof, in any of a variety of prokaryotic expression systems using recombinant DNA techniques which are well known in the art. For a review of such molecular cloning techniques, see Maniatis et al., 1982, Molecular Cloning, A Laboratory Manual, Cold Spring Harbor Laboratory. The ras proteins expressed in such prokaryotic systems will not be processed or post-translationally modified as they would be in eukaryotic systems. Such unprocessed ras products are appropriate substrates for assaying farnesylation and FT activity. Any of a variety of well known prokaryotic expression systems may be used to express unprocessed ras proteins. See, for example, Section 6.1.1, infra, which describes the expression of a number of ras p21 proteins in *E. coli*. Alternatively, since the amino acid sequence of ras proteins is known (Barbacid, 1987, Ann. Rev. Biochem. 56: 779-827) ras protein substrates for use in the assays of the invention may be chemically synthesized using standard chemical methods known in the art (e.g., see Hunkapiller et al., 1986, Nature 310: 105-111). Indeed, any protein or peptide containing the CAAX box motif may be synthesized for use as the CAAX-substrate in the assays of the invention.

Whether produced by molecular cloning methods or by chemical synthetic methods, the amino acid sequence of the unprocessed ras protein substrate which may be used in the assay of the invention need not be identical to the reported sequence of ras. The unprocessed ras protein substrates used in the assay of the invention may comprise altered sequences in which amino acid residues are deleted, added or substituted. Functionally equivalent amino acid residues may be substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the non polar (hydrophobic) amino acids include alanine, leucine, isoleucine, valine, proline phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic and glutamic acid. However modified, the unprocessed ras protein substrate used in the assay should contain the defined carboxy-terminal structure, known as the CAAX box, which is required for farnesylation.

The FT enzyme used in the assay may be obtained from a variety of sources. For example, FT used in the assay may be isolated from any of a variety of mammalian cells, tissues, or organs using the purification schemes described in Section 7, infra, and FIGS. 7-10. Alternatively, crude lysates of cells which express FT, or cytosolic fractions of cells, tissues or orqans that express FT may be utilized as a component in the assay of the invention; e.g., see Section 6.1.2, infra. As explained in Section 6.3.4, infra, all mammalian cells and tissue extracts examined herein demonstrated FT activity, albeit at different levels. Porcine tissues, including brain, kidney and lung appear to be abundant sources of the enzyme. These can be advantageously used to provide for the purified FT, extracts or cytosolic fractions used in the assay.

Once FT is purified to homogeneity, its amino acid sequence can be determined, in whole or part, using standard sequencing techniques, e.g., Edman degradation. (See, for example, Creighton, 1983, Proteins, Structures and Molecular Principles, W.H. Freeman and Co., N.Y., pp. 34-49). These amino acid sequences (whole or partial) may then be used to derive nucleotide coding sequences for FT. These nucleotide sequences, or fragments or functional equivalents thereof, may be used to generate recombinant DNA molecules that direct the expression of the FT gene product, or functionally active peptides or functional equivalents thereof, in appropriate host cells.

Genomic sequences for FT may be obtained from any mammalian cell source, whereas mRNA for preparation of cDNA copies may be obtained from cell sources that produce FT. Alternatively, mammalian cell lines can be used as a convenient source of DNA or RNA.

The FT coding sequence may be obtained by cDNA cloning of RNA isolated and purified from such cellular sources or by genomic cloning. Either cDNA or genomic libraries may be prepared from the DNA fragments generated using techniques well known in the art, including but not limited to the use of restriction enzymes.

The fragments which encode FT may be identified by screening such libraries with a nucleotide probe that is substantially complementary to any portion of the derived FT sequences. To these ends, techniques well known to those skilled in the art for the isolation of DNA, generation of appropriate restriction fragments, construction of clones and libraries, and screening recombinants may be used. For a review of such techniques see, for example, Maniatis et al., 1982, Molecular Cloning A Laboratory Manual, Cold Spring Harbor Press, N.Y., Chapters I-II. Alternatively, oligonucleotides derived from FT amino acid sequences could be used as heterologous primers in PCR (polymerase chain reactions) to generate cDNA or genomic copies of FT sequences from a variety of cellular sources. For a review of such PCR techniques, see for example, Gelfand, D.H., 1989, "PCR Technology. Principles and Applications for DNA Amplification," Ed., H.A. Erlich, Stockton Press, N.Y.; and "Current-Protocols in Molecular Biology," Vol. 2, Ch. 15, Eds. Ausubel et al., John Wiley & Sons, 1988.

In an alternate embodiment of the invention, the coding sequence of the FT gene could be synthesized in whole or in part, using chemical methods well known in the art. See, for example, Caruthers, et al., 1980, Nuc. Acids Res. Symp. Ser. 7:215-233; Crea and Horn, 1980, Nuc. Acids Res. 9(10): 2331; Matteucci and Caruthers, 1980, Tetrahedron Letters 21:719; and Chow and Kempe, 1981, Nuc. Acids Res. 9(12) 2807-2817. Alternatively, the FT protein itself could be produced using chemical methods to synthesize the amino acid sequence in whole or in part. For example, peptides can be synthesized by solid phase techniques, cleaved from the resin, and purified by preparative high performance liquid chromatography. (E.g., see, Creighton, 1983, Proteins Structures and Molecular Principles, W.H. Freeman and Co., N.Y. pp. 50-60). The composition of the synthetic peptides may be confirmed by amino acid analysis or sequencing (e.g., the Edman degradation procedure; see Creighton, 1983, Proteins, Structures and Molecular Principles, W.H. Freeman and Co., N.Y., pp. 34-49).

FPP may be obtained from a variety of commercial sources (e.g., Sigma Chemical Co.; Aldrich Chemical Co.; etc.). As previously explained, either substrate, the CAAX-substrate or FPP, may be labeled with any of a variety of signal generating compounds including radiolabels, fluorogenic compounds, colorimetric compounds, enzymes, etc., using standard metabolic labeling techniques or chemical conjugating techniques. Indeed, radiolabeled FPP ([$^3$H]FPP and [$^{14}$C]FPP) is commercially available (e.g., Amersham; New England Nuclear).

The reaction conditions used in the FT assay may be adjusted to optimize farnesylating activity in vitro. For example, using the reaction conditions described in the examples herein, appropriate concentrations of cations such a $Mg^{2+}$, $Mn^{2+}$ (e.g., see, FIG. 4A and 4B, respectively), or $Cd^{2+}$ may be added to the reaction buffer. Likewise, agents such as DTT, which protect sulfhydryl groups, may be added to the reaction mixture (e.g., see FIG. 4D). Although FT is active at a wide range of pHs, optimal activity may be achieved by adjusting the pH between 6.8 and 8.0 (e.g., see FIG. 4C). Because the FT enzyme is heat labile (FIG. 3C), high temperatures (e.g., 65° C. for 30 minutes) should be avoided during the reaction.

5.2. THE FARNESYL-PROTEIN TRANSFERASE ASSAY

The assay of the invention is accomplished by reacting the CAAX-substrate with the FPP donor in the presence of the FT enzyme. Preferably, the assay is conducted using reaction conditions which favor the farnesylation reaction; e.g., when using the reaction conditions described in the examples infra, the reaction may be conducted in the presence of appropriate concentrations of cations such as $Mg^{2+}$, $Mn^{2+}$ or $Cd^{2+}$; in the presence of a sulfhydryl compound such as DDT; and at an appropriate pH (6.8 to 8) and temperature. Detection of the amount of the farnesyl residue incorporated into the CAAX-substrate is a direct indication of farnesylation and FT activity. Substances which inhibit ras mediated transformation of normal cells to cancer cells may be identified by their ability to inhibit the incorporation of the farnesyl residue into the CAAX-substrate when added into the reaction mixture.

The assay of the invention may be conducted in a liquid phase or a solid-liquid phase. Incorporation of the farnesyl residue into the CAAX-substrate may be assessed in a variety of ways depending upon the reaction format used. Where the assay is conducted in a liquid phase, the farnesylated reaction product may be separated from the reaction mixture at the completion of the reaction by a number of techniques, including but not limited to, chromatographic separation (e.g., thin layer chromatography, high performance liquid chromatography, etc.); electrophoretic methods (such as SDS-PAGE, see, for example, Section 6.2.1, infra). Where a labeled CAAX-substrate or FPP is used, the reaction product may be immobilized onto a solid phase, e.g., by binding to a filter as described in Section 6.2.2, infra or by binding to microtiter wells; by immunoprecipitation using antibodies that bind to the CAAX-substrate without interfering with its CAAX motif; etc. The amount of label incorporated into the isolated reaction product may then be measured as a direct indication of the degree of farnesylation of the CAAX-substrate.

Alternatively, the reaction may be conducted in a solid phase by immobilizing the CAAX-substrate prior to initiating the reaction with FPP in the presence of FT with or without a test substance. In this regard, a number of techniques for immobilization of proteins may be used, including but not limited to immobilization (by covalent or non-covalent attachment) of the CAAX-substrate on a filter, microtiter wells, or beads, etc.; or on a filter, microtiter wells, or beads coated with antibodies that bind to the CAAX-substrate without interfering with its CAAX motif; etc. Upon completion of the reaction of the immobilized CAAX-substrate with FPP in the presence of FT, all unreacted components are removed from the reaction mixture. Where labeled FPP is used, the amount of label incorporated into the immobilized CAAX-substrate is measured as a direct indication of the degree of farnesylation.

The invention also encompases kits which can be used to screen substances to identify those that inhibit farnesylation of ras products and, therefore, transformation by ras oncogenes. Such kits may include the reaction components of the assay; i.e., the CAAX-substrate, the FPP substrate, and FT (purified FT, or cell extracts or cytosolic fractions containing FT). Either substrate contained in the kit may be labeled with a signal generating compound. The kit may also include a reaction buffer formulated to optimize FT reactivity (e.g., a buffer containing appropriate concentrations of cations such as $Mg^{2+}$, $Mn^{2+}$ or $Cd^{2+}$; sulfhydryl protectors such as DTT; and adjusted to an appropriate pH (e.g., ranging between 6.8 to 8). The kit may also include the vessels used to conduct the reaction; the immobile phase used to immobilize the reaction product or the CAAX-substrate, etc.

6. EXAMPLE: ASSAY FOR FARNESYL-PROTEIN TRANSFERASE

The subsections below describe assays that can be used to detect FT enzyme activity in which unprocessed ras proteins are used as the CAAX-substrate.

6.1. MATERIALS AND METHODS

6.1.1. Purification of H-ras p21 Proteins

Bacterial expression vectors driven by the bacteriophage $\lambda$ $P_L$ promotor controlled by trans expression of the temperature-sensitive cIts repressor have been described (Crowl et al., 1985, Gene 38: 31-38). Such expression vectors carrying retroviral H-ras sequences were used to transform E. coli cells strain C600 (pRK248cIts) which carry the cIts repressor gene in a low copy plasmid (pRK248) compatible with pBR322-derived vectors. These cells can produce high levels of H-ras p21 proteins when shifted from the non-permissive (30° C.) to the permissive (42° C.) temperature. Using this system, both wild type and mutant H-ras p21 proteins listed in Table I, below, were cloned and expressed in E. coli.

TABLE I

| H-ras PROTEIN | H-ras p21 PROTEINS UTILIZED IN EXAMPLES | | |
|---|---|---|---|
| | CARBOXY-TERMINAL SEQUENCE[a] | GDP/GTP BINDING | FOCUS FORMATION |
| WILD TYPE | | | |
| p21N | —$Cys^{186}$—$Val^{187}$—$Leu^{188}$—$Ser^{189}$ | Yes | No |
| p21T | —$Cys^{186}$—$Val^{187}$—$Leu^{188}$—$Ser^{189}$ | Yes | Yes |
| p21H | —$Cys^{186}$—$Val^{187}$—$Leu^{188}$—$Ser^{189}$ | Yes | Yes |
| MUTANTS | | | |
| pNW858 | —$Ser^{186}$—$Val^{187}$—$Leu^{188}$—$Ser^{189}$ | Yes | No |
| pNW277 | —$Cys^{186}$—$Thr^{187}$—$Pro^{188}$ | Yes | No |
| pNW754 | -[Δ166-186]-$Val^{187}$—$Leu^{188}$—$Ser^{189}$ | Yes | No |
| pNW739 | -[Δ166-179]-$Cys^{186}$—$Val^{187}$—$Leu^{188}$—$Ser^{189}$ | Yes | Yes |

[a]Mutated amino acid residues are indicated in bold-faced type.

These H-ras p21 proteins were partially purified as previously described (Hattori et al., 1985, Mol. Cell. Biol. 6: 1449-1455). Briefly, E. coli cells were suspended in 5 volumes of Buffer A (50 mM Tris-HCl, pH 7.5, 50 mM NaCl, 1 mM $MgCl_2$, 10 mM β-mercaptoethanol and 5% glycerol) and sonicated on ice for 30 seconds at 1 minute intervals for a total of 6 times. The sonicated extract was centrifuged at 10,000× g for 30 minutes and the supernatant was further clarified by centrifugation at 150,000× g for 1 hour The supernatant was brought to 48% saturation with saturated ammonium sulfate and stirred for 16 hours at 4° C. The precipitate was collected by centrifugation at 20,000× g and dissolved in buffer B (20 mM Tris-HCl, pH 8.0, 10 mM NaCl, 10 mM β-mercaptoethanol, 25% glycerol). The sample was extensively dialyzed against buffer B for 48 hours and purified on a DEAE-Sephacel Column. Fractions containing H-ras p21 proteins were pooled and concentrated by filtration through a YM-10 membrane (Amicon). Mutant H-ras p21 proteins (pNW 277, pNW 858, pNW 754, pNW 739; see Table I) were purified through the ammonium sulfate fractionation step. Each of the H-ras p21 protein preparation were tested by Westerns blot analysis with the anti-ras Y13-259 monoclonal antibody and for [$^3$H]GDP binding activity as previously described (Manne et al., 1984, Proc. Natl. Acad. Sci. 81: 6953–6957).

6.1.2. CELL AND ORGAN EXTRACTS

Murine NIH3T3 cells transformed by either the human T24 H-ras oncogene (44-911 cell line; Pulciani et al., 1982, Proc. Natl. Acad. Sci. 79: 2845–2849) or an amplified H-ras proto-oncogene (115-611 cell line; Pulciani et al., 1985, Mol. Cell. Biol. 5: 2836–2841) were grown in Dulbecco's modified Eagle's medium supplemented with 10% calf serum. Human medullary thyroid carcinoma cells (TT cell line) infected with the Harvey strain of murine sarcoma virus (MSV) were propagated as previously described (Nakagawa et al., 1987, Proc. Natl. Acad. Sci. 84: 5923–5927).

Tissue culture cells were washed with ice cold phosphate buffered saline (PBS) and incubated at 4° C. for 30 minutes in buffer C (10 mM Hepes, pH 7.4, 1 mM $MgCl_2$, 1 mM EGTA). Cells were collected and sonicated 5 times for 30 second periods with intermittent cooling of the probe. The extract was centrifuged at 10,000× g for 10 minutes and the supernatant was further centrifuged at 100,000× g for 60 minutes at 4° C. The membranous pellet fraction (P-100) was re-suspended in PBS and gently sonicated to obtain uniform vesicles. The supernatant (S-100) was concentrated approximately 10 fold by ultrafiltration. Both S-100 and P-100 fractions were stored in small aliquots in liquid nitrogen.

Various organs including brain, heart, kidney, liver, and lung, were surgically removed from a pig, immediately placed at 4° C. and processed within 2 hours. The organs were rinsed, cut into small pieces, and homogenized in a Waring blender with 4 volumes of buffer D (25 mM Tris-HCl, pH 7.4, 1 mM DTT, 1 mM $MgCl_2$, 1 mM EDTA, 1 mM EGTA, and 1 mM PMSF). The homogenate was centrifuged at 10,000× g for 10 minutes, the supernatant passed through 4 layers of cheese cloth and centrifuged at 100,000× g for 1 hour at 4° C. The S-100 soluble fraction was stored in small aliquots in liquid nitrogen. The amount of protein was determined by the method of Bradford using bovine serum albumin as the standard (Bradford, 1976, Anal. Biochem. 72: 248–254).

6.2. ASSAYS FOR FARNESYL-TRANSFERASE ACTIVITY

6.2.1. SDS-Page Assay

One to three micrograms of partially purified H-ras p21 protein (Table I) were mixed with various amounts of cell or organ extract in a 100 mM Hepes, pH 7.4, buffer containing 25 mM $MgCl_2$ and 10 mM DTT at 4° C. in a total volume of 10 μl, unless otherwise stated. The reaction was initiated by the addition of 1 μl of 10 μM [$^3$H]FPP (specific activity 20 Ci/mmol, New England Nuclear) and incubated at 37° C. for the indicated length of time. The reaction was terminated by the additon of 12 μl of 2× SDS-PAGE sample buffer (125 mM Tris-HCl, pH 6.8, 20% glycerol, 10% β-mercaptoethanol and 0.0025% bromophenol blue). Samples were boiled and analyzed by SDS-PAGE in 12.5% gels. The electrophoresed gels were fixed in 15% methanol and 7.5% acetic acid for 30 minutes, treated with Enlightening (NEN), dried and exposed to Kodak X-Omatic AR5 film in the presence of intensifier screens at −70° C. for various periods of time. The amount of radioactivity present in the labeled p21 proteins were determined by cutting the band from the gel, followed by solubilization and liquid scintillation counting in a TriCarb Model 2200 CA Liquid Scintillation Counter.

6.2.2. FILTER BINDING ASSAY

Since the SDS-PAGE analysis of FT activity is rather time consuming, we developed a rapid filter binding assay. The assay conditions for FT activity were the same as those described above. Alternatively, the reaction could be stopped by placing the reaction mixture on ice and adding 200 μl of buffer G (20 mM Tris HCl, pH 8.0, 100 mM NaCl, 1 mM DTT, 10 mM $Na_2HPO_4$, and 10 mM sodium pyrophosphate). Samples were filtered through BA85 nitrocellulose filters, (presoaked in buffer G) under vacuum and the tubes were rinsed once with 20 μl buffer G. The filters were then washed with 12 ml of buffer G, placed in glass scintillation vials, dissolved in 1 ml of methylcellosolve, and counted in a TriCarb Model 2200CA Liquid Scintillation Counter after addition of 10 ml of hydrofluor scintillation liquid. The use of this filter binding assay to measure farnesyl transferase activity is illustrated in FIG. 1 which shows the linear response of the assay as the concentration of enzyme protein is increased. The equivalence of the SDS-PAGE assay and Filter Binding assay was demonstrated by using both methods to determine the farnesyl transferase activity present in fractions derived from of a Sephacryl S-200 gel filtration column used to fractionate a partially purified porcine kidney cell extract (FIG. 2). Similar results were observed with either method.

6.3. RESULTS

6.3.1. In Vitro Farnesylation of H-Ras p21 Proteins

We reasoned that ras p21 proteins expressed in bacteria are unlikely to be processed, thus providing adequate substrates for assaying those enzymes involved in the post-translational modification of their carboxy-terminus. Therefore, we partially purified a series H-ras p21 proteins expressed in *E. coli* cells which included p21T and p21H, the products of the v-H-ras oncogenes present in the BALB and Harvey strains of MSV, respectively (Table I). In addition, we used a modified BALB-MSV H-ras p21 protein in which its 12th residue lysine was converted into a glycine. The resulting protein, designated H-ras p21N, has an amino acid sequence identical to the products of the human and rat H-ras proto-oncogenes (except for Lys[143]) and no longer possesses transforming properties. Each of these proteins was shown to be biochemically active by their ability to bind [$^3$H]GDP.

Recent studies have indicated that farnesyl is the isoprenyl unit linked to the carboxy-terminus of ras proteins and that the likely donor molecule responsible for their farnesylation is FPP. Therefore, our farnesyl-protein transferase assay was based on the incorporation of [$^3$H]FPP into bacterially synthesized H-ras p21 proteins in the presence of crude lysates obtained from various human and mouse cell lines.

FIG. 3 depicts a representative experiment in which a partially purified preparation of H-ras p21N was incubated with a crude extract of TT cells, a human medullary thyroid carcinoma cell line transformed in culture with the v-H-ras oncogene. We selected H-ras transformed cells because they should contain the necessary H-ras p21 processing enzymes, including the putative farnesyl-protein transferase. Addition of [$^3$H]FPP to this reaction mixture resulted in the specific labeling of a single protein of about 23 kDa (FIG. 3A). Labeling of this protein was dependent upon the presence of both the bacterially-expressed H-ras p21N protein and the TT cell lysate (FIG. 3A).

Fractionation of the crude extract derived from human TT cells into soluble (S-100) and membranous (P-100) fractions revealed that the H-ras p21 farnesylating activity was almost entirely detected in the soluble cytosolic fraction (FIG. 3B). Since the activity was mostly detected in the S-100 fraction, and the P-100 membrane fraction had little or no activity, soluble S-100 fractions were utilized in subsequent studies.

Pre-incubation of the S-100 fraction of TT cells at 65° C. for 30 minutes completely abolished the incorporation of [$^3$H]FPP into H-ras p21N (FIG. 3C). These results suggest that the observed H-ras p21N farnesylation is catalyzed by a heat-labile enzyme. To illustrate the specificity of this enzymatic activity, we incubated that reaction mixture with an excess of non-radioactive FPP. As shown in FIG. 3C, incorporation of [$^3$H]FPP into H-ras p21N was completely abolished. Finally, we examined whether the soluble S-100 TT cell extract also catalyzed the farnesylation of the transforming H-ras isoforms p21T and p21H. As shown in FIG. 3D, each of these bacterially-synthesized H-ras p21 proteins became farnesylated with comparable efficiencies, indicating that this reaction is independent of of the activated (oncogenic) state of H-ras proteins. As a control, unrelated molecules such as Il-2 and p75$^{myb}$ expressed in $E.$ $coli$ cells under the control of the same $P_L$-derived vector utilized to express the H-ras p21 proteins, did not become farnesylated when used as substrates in the same assay (FIG. 3D). In addition, when IL-2 or p75$^{myb}$ were used as substrates, or when crude extracts of $E.$ $coli$ cells expressing other recombinant proteins (e.g., interferon) were used as substrates, we did not detect incorporation of label from [$^3$H]FPP into any 23 kDA protein. These results indicate that this assay detects the specific incorporation of farnesyl residues into H-ras p21 proteins by a farnesyl-protein transferase activity.

6.3.2. CHARACTERIZATION OF FARNESYL-PROTEIN TRANSFERASE ACTIVITY

As shown in FIG. 4, the in vitro farnesylating activity under the reaction conditions used in the present examples required the presence of certain divalent cations such as $Mg^{2+}$, $Mn^{2+}$, or $Cd^{2+}$. In contrast, $Ca^{2+}$, $Zn^{2+}$, $Pb^{2+}$, $Ba^2$, $Cu^{3+}$, $Fe^{2+}$, $Fe^{3+}$, $Cu^{2+}$, $Hg^{2+}$ or $Li^{2+}$ ions were ineffective in supporting the in vitro farnesylation of H-ras p21 proteins. In the case of $Mg^{2+}$, the optimal concentration was 25 mM (FIG. 4A), whereas the requirements of appeared to be much lower since optimal activity was observed at 0.5 mM (FIG. 4B). Addition of monovalent ions such as Na$^+$ (100 mM) or F$^-$ (10 mM) had no effect on the reaction. Farneyslation of $E.$ $coli$-synthesized H-ras p21 proteins appears to require agents known to protect sulfydryl groups, such as DTT, at considerably high concentrations (FIG. 4D), and can take place at a relatively wide range of pHs resulting in optimal activity between pH 6.8 and pH 8.0 (FIG. 4C).

Next, we determined the kinetics of this in vitro farnesylating activity. As shown in FIG. 5, the reaction is linear with time (up to one hour) and enzyme concentration, and reaches saturation when the concentrations of the two substrates, H-ras p21 and [$^3$H]FPP are increased in the assay. Other characteristics in this in vitro farnesylation reaction include the lack of an external source of energy, since the addition of ATP or GTP did not have any effect on the incorporation of [$^3$H]FPP on H-ras p21. Similarly, extensive dialysis of the TT S-100 extract did not result in significant loss of activity, suggesting that the putative farnesyl-protein transferase does not require small co-factors (10,000 daltons) for proper activity, unless they are tightly bound to the enzyme.

6.3.3. SPECIFICITY OF H-ras p21 FARNESYLATION

Farnesylation of H-ras p21 proteins in vivo is known to take place in a cysteine residue located at position 186, just three residues from the carboxy-terminus. In order to determine whether the above in vitro farnesylating activity occurred at this specific residue, we utilized a mutated isoform of the transforming H-ras p21H protein in which the Cys$^{186}$ residue had been replaced by Ser$^{186}$. As a consequence of this mutation, the resulting protein, designated pNW858 (Table I), can no longer interact with the inner side of the plasma membrane and lacks transforming activity. As shown in FIG. 6, lane b this mutant H-ras 21H$^{S186}$ protein did not become farnesylated in the in vitro assay. Similar results were obtained with a second H-ras p21H mutant, known as pNW277 (Table I), in which the three wild type carboxy-terminal residues Val-Leu-Ser were replaced by Thr-Pro (FIG. 6, lane e). These three wild type residues are part of the CAAX box motif required for proper posttranslational modification and membrane interaction of ras p21 proteins in vivo.

Genetic studies have shown the farnesylation of ras p21 proteins requires an intact CAAX box. A partially purified transforming H-ras p21H mutant protein, known as pNW739, in which amino acid residues 166 to 179 had been deleted became efficiently farnesylated (FIG. 6, lane c). However, a similar H-ras p21H mutant protein (pNW754) in which the deletion extended to residue 186, the presumed target of farnesylation, did not incorporate detectable amounts of [$^3$H]FPP (FIG. 6, lane d). These results illustrate that in vitro farnesylation of H-ras p21 proteins specifically occurs at the physiological Cys$^{186}$ residue. Moreover, they indicate that the enzyme responsible for this reaction recognizes the same H-ras p21 structure required for proper posttranslational processing of ras p21 molecules in vitro. These findings, taken together, strongly indicate that the enzyme identified in these S-100 porcine tissue extracts is a farnesyl-protein transferase (FT).

6.3.4. FARNESYL-PROTEIN TRANSFERASE ACTIVITY IN MAMMALIAN CELLS AND TISSUES

Next, we searched for this H-ras p21 farnesylating activity in a variety of mammalian cell lines and tissues in order to obtain an abundant source of this enzymatic activity. As summarized in Table II, this H-ras p21 farnesylating activity was found in all mammalian cells and tissue extracts that we examined, albeit at different levels. For instance, porcine tissues including brain, kidney and lung appeared to possess the highest levels of activity (Table II). In all cases, farnesylation of H-ras p21 proteins in vitro was only observed with the corresponding S-100 soluble fraction, suggesting that the putative farnesyl-protein transferase detected in this assay is a cytoplasmic enzyme. Based on these results, S-100 extracts of porcine brain and kidney tissue were subsequently used throughout the studies described herein.

TABLE II
FARNESYL-PROTEIN TRANSFERASE ACTIVITY IN VARIOUS CELLS AND TISSUES

| SOURCE OF S-100 EXTRACT | FARNESYL TRANSFERASE ACTIVITY[a] (pmoles of [$^3$H]FPP/mg/hr) |
|---|---|
| CELL LINES | |
| 44-911 | 2.7 |
| 115-611 | 6.4 |
| TT | 18.0 |
| TISSUES | |
| Human Platelets | 9.9 |
| Procine Adrenal Medulla | 44.0 |
| Procine Brain | 62.0 |
| Procine Heart | 18.0 |
| Procine Kidney | 78.0 |
| Procine Liver | 14.0 |
| Procine Lung | 53.0 |

[a]1.25 μg of partially purified H-ras p21N were incubated at 37° C. for 1 hours with 20-30 μg of the corresponding S-100 extract. The amount of [$^3$H]FPP incorporated into H-ras p21 proteins was determined by SDS-PAGE analysis as described in Materials and Methods.

7. EXAMPLE: PURIFICATION OF FARNEYSL PROTEIN TRANSFERASE

The subsections below describe two methods for the partial purification of FT from porcine kidneys.

7.1. PARTIAL PURIFICATION OF FARNESYL PROTEIN TRANSFERASE FROM PORCINE KIDNEY: DE-52 CHROMATOGRAPHY

Porcine kidney S-100 fractions were passed through a cheesecloth two times and subjected to ammonium sulfate fractionation as outlined in the scheme depicted in FIG. 7. These various ammonium sulfate fractions were dialyzed extensively against buffer E (20 mM Tris HCl, pH 7.4, 1 mM DTT, 0.1 mM EDTA, 0.5 mM PMSF and 5% glycerol) and tested for farnesyl protein transferase activity by the SDS-PAGE and filter binding assays. The results, summarized in Table III, indicate that most of the FT activity could be found in the 30–40% and in the 40–55% fractions. We utilized the 30–40% ammonium sulphate fraction for subsequent purification steps.

TABLE III
FARNESYL-PROTEIN TRANSFERASE (FT) ACTIVITY IN THE VARIOUS AMMONIUM SULPHATE FRACTIONS

| FRACTION | TOTAL FT ACTIVITY[a] (SDS-PAGE ASSAY) | TOTAL FT ACTIVITY[b] (Filter ASSAY) | TOTAL VOLUME (ml) |
|---|---|---|---|
| Kidney S-100 Extract | 63.9 (100%) | 63.5 (100%) | 270 |
| Fraction | | | |
| 0–30% | 0.2 (0%) | 2.0 (3%) | 6 |
| 30–40% | 8.6 (13%) | 24.4 (38%) | 14 |
| 40–55% | 11.7 (18%) | 23.3 (37%) | 78 |
| 55–80% | 6.0 (9%) | 12.0 (19%) | 38 |
| 80% | 0 (0%) | 6.0 (11%) | 320 |

[a]Farnesyl-protein transferase (FT) activity measured by the SDS-PAGE assay is expressed as nmoles of [$^3$H]FPP incorporated into ras p21 protein. Results are the average of two experiments.
[b]Farnesyl-protein transferase (FT) activity measured by the Filter Binding assay is expressed as nmoles of [$^3$H]FPP bound to the filter in the presence of enzyme. Results are the average of two experiments.

The 30–40% ammonium sulfate fraction was loaded onto a DE-52 column (1.6 cm × 30 cm) equilibrated with buffer E. The column was washed with buffer E until the $A_{280}$ of the eluate reached approximately 0.05 units. Bound proteins were eluted with 410 ml of a linear gradient of 0 to 0.6 M NaCl in buffer E. Finally, the column was washed with buffer E containing 1 M NaCl. FIG. 8 shows the elution profile. The filter binding assay described in Section 6.2.2. was used to quickly locate the farnesyl transferase activity. These results were confirmed by the more rigorous SDS-PAGE analysis described in Section 6.2.1. (FIG. 8). Active fractions were pooled and concentrated by pressure ultrafiltration using Amicon YM-10 membranes to about 2 ml and submitted to a second purification step using gel filtration chromatography.

7.2. PARTIAL PURIFICATION OF FARNESYL-PROTEIN TRANSFERASE FROM PORCINE KIDNEY: GEL FILTRATION CHROMATOGRAPHY

A Superose 6 HR 10/30 column was equilibrated with buffer F (50 mM sodium phosphate, pH 7.0, 200 mM NaCl, 1 mM DTT, 5% glycerol) and calibrated with thyroglobulin, ferritin, catalase, aldolase, bovine serum albumin, cytochrome C, yeast-alcohol dehydrogenase, β-amylase, carbonic anhydrase, cytochrome C and glycyl-tyrosine. Chromatography was performed using Pharmacia FPLC system and a 200 μl sample loop. Samples (200 μl) containing either calibration markers or farnesyl-protein transferase purified through DE-52 cellulose chromatography (Section 7.1., supra) were injected onto the Superose 6 HR 10/30 column and eluted with buffer F at a flow rate of 0.2 ml/minute. Fractions (0.2 ml) were collected and assayed for farnesyl-protein transferase activity by both SDS-PAGE and filter binding assays. FIG. 9 shows the $A_{280}$ profile and the activity profile as determined by the SDS-PAGE assay. Most of the activity eluted as a broad peak in the molecular weight range of 350 to 120 kDa. Two defined peaks of activity corresponding to molecular weights of 300 kDA and 130 kDa could be identified within this broad area. Three explanations are possible: (a) the smaller molecular weight enzyme may correspond to a proteolytic fragment of the larger one; (b) the larger form may represent a multi-protein complex; or (c) several farnesyl-protein transferases may be present in this porcine kidney extract.

The farnesyl-protein transferase activity partially purified by DE-52 cellulose (Section 7.1., supra) was also submitted to gel filtration chromatography using a different resin, Sephacryl S-200. The results were very similar to those described above for the Superose 6 HR 10/30 column. As shown in FIG. 10, the farnesyl-protein transferase activity also eluted as two distinct peaks within a broad area, independently of whether we used the SDS-PAGE or the filter binding assay. The estimated molecular weights of these peaks based on the elution of the same molecular weight markers used to calibrate the Superose 6 column, were 250 kDa and 90 kDa. When fractions containing the highest farnesyl-protein transferase activity (from both Superose 6 and Sephacryl S-200 columns) were analyzed by SDS-PAGE followed by silver staining, multiple protein species were observed indicating that further purification steps will be required to isolate farnesyl-protein transferase in pure form.

What is claimed is:

1. An assay for identifying compounds that inhibit ras oncogene activity, comprising:
    (a) reacting a protein or peptide substrate having a CAAX motif with farnesyl pyrophosphate and farnesyl-protein transferase in the presence of a test substance; and
    (b) detecting whether the farnesyl residue is incorporated into the protein or peptide substrate, in which the ability of the test substance to inhibit ras oncogene activity is indicated by a decrease in the incorporation of the farnesyl residue into the protein or peptide substrate as compared to the amount of the farnesyl residue incorporated into the protein or peptide substrate in the absence of the test substance.

2. The assay according to claim 1 in which the protein or peptide substrate comprises an unprocessed ras protein.

3. The assay according to claim 1 in which the protein or peptide substrate comprises an unprocessed mutant ras protein containing the CAAX motif.

4. The assay according to claim 1 in which the protein or peptide substrate comprises a portion of an unprocessed ras protein containing the CAAX motif.

5. The assay according to claim 1 in which the protein or peptide substrate comprises a portion of an unprocessed mutant ras protein containing the CAAX motif.

6. The assay according to claim 1 in which the protein or peptide substrate comprises a peptide having at least six amino acid residues containing the CAAX motif.

7. The assay according to claim 1 in which the protein or peptide substrate is labeled with a signal-generating compound.

8. The assay according to claim 1 in which the farnesyl pyrophosphate is labeled with a signal-generating compound.

9. The assay according to claim 7 or 8 in which the signal-generating compound comprises a radiolabel, a fluor, an enzyme or a colorimetric signal-generating compound.

10. The assay according to claim 1 in which the farnesyl-protein transferase employed is one which has been at least partially purified.

11. The assay according to claim 1 in which the farnesyl-protein transferase in contained within an extract of a cell that produces farnesyl-protein transferase.

12. The assay according to claim 1 in which the farnesyl-protein transferase is contained within a cytosolic fraction of a cell which produces farnesyl-protein transferase.

13. The assay according to claim 1 in which the reaction is conducted in the presence of $Mg^{2+}$, $Mn^{2+}$ or $Cd^{2+}$.

14. The assay according to claim 1 in which the reaction is conducted in the presence of dithiothreitol.

15. The assay according to claim 1 in which the reaction is conducted at a pH within the range of about 6.8 to about 8.

16. The assay according to claim 1 in which the reaction is conducted in a liquid phase to form a reaction product which is separated from the reaction mixture upon completion of the reaction.

17. The assay according to claim 16 in which the reaction product is immobilized on a filter.

18. The assay according to claim 16 in which the reaction product is isolated by SDS-polyacrylamide gel electrophoresis.

19. The assay according to claim 1, 7 or 8 in which the protein or peptide substrate is immobilized prior the reaction so that the reaction is conducted in a solid-liquid phase.

* * * * *